United States Patent [19]

Watson et al.

[11] Patent Number: 5,496,826
[45] Date of Patent: Mar. 5, 1996

[54] PHARMACEUTICAL METHODS OF USING HETEROCYCLIC DERIVATIVES OF N-PHENYLAMIDES

[75] Inventors: Brett T. Watson, Wallingford; Astrid A. Ortiz, Fairfield, both of Conn.

[73] Assignee: Bristol-Myers Squibb Company, Princeton, N.J.

[21] Appl. No.: 300,671

[22] Filed: Sep. 2, 1994

[51] Int. Cl.$^6$ .............. A61K 31/44; A61K 31/425; A61K 31/42; A61K 31/415
[52] U.S. Cl. .......... 514/303; 514/301; 514/302; 514/367; 514/375; 514/394; 546/113; 546/114; 546/115; 546/116; 546/118; 548/152; 548/178; 548/224; 548/310.7
[58] Field of Search ................... 548/310.7, 224, 548/152, 310.7, 224, 152, 178; 546/113, 118; 514/303

[56] References Cited

U.S. PATENT DOCUMENTS

| | | | |
|---|---|---|---|
| 3,586,670 | 6/1971 | Brenneisen et al. | 260/240 |
| 3,624,100 | 11/1971 | Frick et al. | 260/309.2 |
| 3,669,979 | 6/1972 | Freyermuth | 260/304 |
| 4,038,396 | 7/1977 | Shen et al. | 424/256 |
| 4,540,648 | 9/1985 | Scheler | 430/172 |
| 4,629,740 | 12/1986 | Robertson | 514/620 |
| 4,632,939 | 12/1986 | Beedle et al. | 514/619 |
| 4,638,014 | 1/1987 | Clark | 514/619 |
| 4,684,748 | 8/1987 | Robertson | 514/619 |
| 4,925,853 | 5/1990 | Smith et al. | 514/338 |
| 4,981,866 | 1/1991 | Beedle et al. | 514/399 |
| 5,151,446 | 9/1992 | Horn et al. | 514/617 |
| 5,276,051 | 1/1994 | Lesieur et al. | 514/415 |

FOREIGN PATENT DOCUMENTS

| | | |
|---|---|---|
| 0447285A1 | 9/1991 | European Pat. Off. . |
| 0506539A1 | 9/1992 | European Pat. Off. . |
| 0520200A2 | 12/1992 | European Pat. Off. . |

*Primary Examiner*—Johann Richter
*Assistant Examiner*—Laura L. Stockton
*Attorney, Agent, or Firm*—Sandra M. Nolan

[57] ABSTRACT

New central nervous system agents conform to formula I:

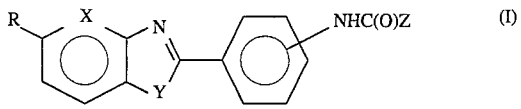

wherein
R=H or $C_{1-4}$ alkoxy;
X=CH or N;
Y=NH, O or S;
Z=$C_{1-4}$ alkyl, $C_{3-6}$ cycloalkyl, $C_{2-3}$ alkenyl, $NH_2$, $C_{1-4}$ alkylamino, or $C_{1-4}$ alkoxyalkyl, with the proviso that Z may not be $CH_3$ when R=H, X=CH, and Y=NH and Z may not be $CH_3$ when R=H, X=N and Y=NH and NHC(O)Z is in the para- position.

24 Claims, No Drawings

PHARMACEUTICAL METHODS OF USING HETEROCYCLIC DERIVATIVES OF N-PHENYLAMIDES

BACKGROUND OF THE INVENTION

This application discloses novel N-phenylamides having 4-heterocyclic substituents. These compounds have activity as anticonvulsants, i.e. anticonvulsive agents, which provide relief for patients suffering from seizures, such as those caused by epilepsy. The novel compounds of the invention also have melatonergic properties.

New anticonvulsants with greater selectivity and lower toxicity are desirable due to the incidence of unwanted side effects and the failure of marketed anticonvulsants to provide significant relief for about one-third of the patient population.

Certain benzimidazoles, e.g., 2-(substituted phenyl)benzimidazoles, have been shown to have sedative activity. I. Yilden et al, in *J. Fac. Pharm. Gazi Univ.*,7, pp. 111–24 (1990) disclose compounds of formula A:

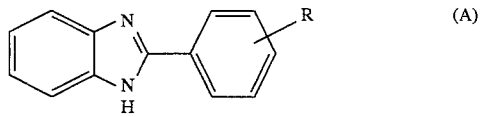

in which R may be $CH_3$, $OCH_3$, Cl, $NO_2$ or para-$NHC(O)CH_3$. The preparation of the ortho- and meta-$NHC(O)CH_3$ compounds was described in *Chemische Berichte*, 32, p. 1469 (1899) and *Chemische Berichte*, 34, p. 2961 (1901) respectively, however, no utility was disclosed.

The preparation and use of N-[4-(1H-imidazo[4,5-b]pyridin-2-yl)phenyl]acetamide (B) as an intermediate has been disclosed by Kutter et al in a German patent application (DE 2305339).

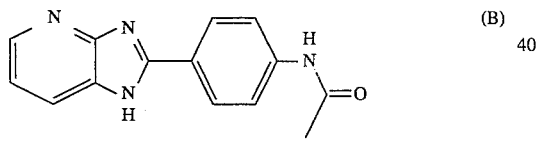

D. Lesieur et al disclosed, in U.S. Pat. No. 5,276,051, certain arylethylamine derivatives that may be used to treat melatonergic disorders and that have anxiolytic, antipsychotic and analgesic properties. These compounds are of formula C:

in which Ar is indolyl-3-yl or another benzoheterocyclic group, $R_1$ is an acyl group and $R_2$ is H or $C_{1-6}$ alkyl.

Among the compounds described by Lesieur et al is a compound of formula D:

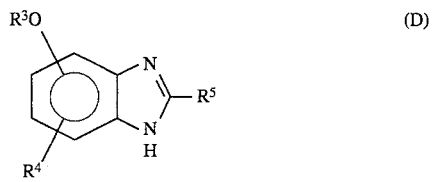

wherein $R_3$ can be H or $C_{1-6}$ alkyl; $R_4$ can be H and $R_5$ can be substituted phenyl or phenylalkyl (containing a $C_{1-3}$ alkyl group). However, the Lesieur reference does not suggest the novel anticonvulsant amides of the present invention.

O. Axelsson et al disclosed, in European Patent Application (EP 0520200 A2), certain 1-(substituted phenyl)-2-(substituted amino) benzimidazoles which may be used to block N-or L-type calcium channels in mammals and for the treatment of central nervous system disorders such as migraine and epilepsy. These compounds are of formula E:

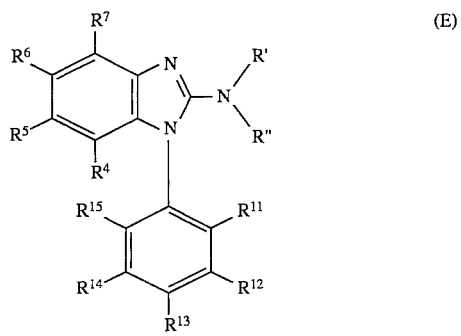

but no phenylamide moiety is described for E.

SUMMARY OF THE INVENTION

Applicants have discovered a novel series of anticonvulsant heterocyclic derivatives of N-phenylamides which conform to formula I:

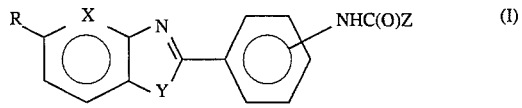

wherein
R=H or $C_{1-4}$ alkoxy;
X=CH or N;
Y=NH, O or S;
Z=$C_{1-4}$ alkyl, $C_{3-6}$ cycloalkyl, $C_{2-3}$ alkenyl, $NH_2$, $C_{1-4}$ alkylamino, or $C_{1-4}$ alkoxyalkyl, with the proviso that Z may not be $CH_3$ when R=H, X=CH, and Y=NH and Z may not be $CH_3$ when R=H, X=N and Y=NH and NHC(O)Z is in the para- position.

Compounds of formula I, as well as pharmaceutically acceptable salts thereof, are described herein as useful in compositions and methods for the anticonvulsive and melatonergic uses.

The anticonvulsive agents of the invention have advantages over similar agents. They perform significantly better in maximal electroshock (MES) tests than reference compounds, e.g., phenobarbital and valproic acid.

In anticonvulsant studies using pentylenetetrazol (PTZ)-induced seizure techniques, these compounds generally improve length of survival or delay initial twitch or seizure responses.

Use of effective amounts of the novel compounds of the invention in compositions and methods eliciting anticonvulsive or melatonergic effects in mammals in need of such treatment is discussed herein.

These and other advantages will become apparent after consideration of the specification and claims.

DETAILED DESCRIPTION OF THE INVENTION

The anticonvulsant agents described herein conform to formula I or are pharmaceutically acceptable salts or hydrates thereof:

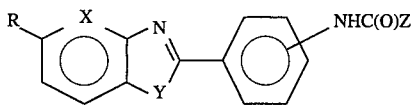

(I)

wherein
R=H or $C_{1-4}$ alkoxy;
X=CH or N;
Y=NH, O or S;
Z=$C_{1-4}$ alkyl, $C_{3-6}$ cycloalkyl, $C_{2-3}$ alkenyl, $NH_2$, $C_{1-4}$ alkylamino, or $C_{1-4}$ alkoxyalkyl, with the proviso that Z may not be $CH_3$ when R=H, X=CH, and Y=NH and Z may not be $CH_3$ when R=H, X=N and Y=NH and NHC(O)Z is in the para- position.

R is generally H or $C_{1-4}$ alkoxy. It is preferably H or $OCH_3$.

X may be CH or N, with CH preferred.

Y is generally NH, O or S, but is preferably NH or O, most preferably NH.

Z can be $C_{1-4}$ alkyl, $C_{3-6}$ cycloalkyl, $C_{2-3}$ alkenyl, $NH_2$, $C_{1-4}$ alkylamino, or $C_{1-4}$ alkoxyalkyl, with the proviso that Z may not be $CH_3$ when R=H, X=CH, and Y=NH and Z may not be $CH_3$ when R=H, X=N and Y=NH and NHC(O)Z is in the para position. Some preferred Z groups are $C_{2-4}$ alkyl, $C_{1-4}$ alkyl amino and $C_{1-4}$ alkoxyalkyl groups, most preferably $C_2H_5$, $NHCH_3$ and $CH_2OCH_3$ groups.

In some preferred embodiments, NHC(O)Z is in the ortho or meta position of the phenyl group and Z is $CH_3$.

In some preferred compounds, X is CH and Z is $CH_3$, $C_2H_5$, $NHCH_3$ or $CH_2OCH_3$.

In still another group of preferred compounds, R is H or $OCH_3$ and Z is $CH_3$ or $CH_2OCH_3$.

By "alkenyl" is meant alkyl groups containing a carbon-carbon double bond. "$C_{2-3}$ alkenyl" groups include $CH=CH_2$, $CH=CH-CH_3$, and $C(CH_3)=CH_2$.

The phrases "alkylamino" and "alkoxyalkyl" refer, respectively, to NH-alkyl and alkylene-O-alkyl groups, in which the alkyl and alkylene moieties contain from 1 to 4 carbon atoms. Preferred groups include $NHCH_3$ and $CH_2OCH_3$.

Preferred compounds of formula I have the amido group in the ortho-or meta- position of the phenylalkyl moiety.

In highly preferred embodiments, compounds of formula I have the amido group in the ortho- and meta position of the phenyl ring, i.e. the NHC(O) Z group is in position 1 or 2 as shown here:

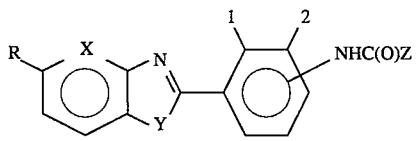

All substituents have the definitions given for formula I, as above.

These preferred embodiments include:
N-[2-(1H-benzimidazol-2yl)phenyl]-N'-methyl urea,
N-[2-(5-methoxy-1H-benzimidazol-2-yl)phenyl]acetamide,
N-[2-(1H-benzimidazol-2-yl)phenyl]propanamide,
N-[2-(benzthiazol-2-yl)phenyl]acetamide,
N-[2-(benzoxazol-2-yl)phenyl]acetamide,
N-[2-(benzoxazol-2-yl)phenyl]-N'-methyl urea,
N-[2-(1H-benzimidazol-2-yl)phenyl]methoxyacetamide,
N-[2-(5-methoxy-1H-benzimidazol-2-yl )phenyl]methoxyacetamide,
N-[2-(5-methoxybenzoxazol-2-yl)phenyl]-N'-methyl urea,
N-[2-(5-methoxybenzoxazol-2-yl)phenyl]acetamide,
N-[2-(5-methoxybenzthiazol-2-yl)phenyl]acetamide,
N-[2-(5-methoxy-1H-benzimidazol-2-yl)phenyl]propanamide,
N-[2-(5-methoxy-1H-benzimidazol-2-yl)phenyl]-N'-methyl urea,
N-[2-(1H-benzimidazol-2-yl)phenyl]cyclopropane carboxamide,
N-[2-(5-methoxy-1H-benzimidazol-2-yl)phenyl]cyclopropane, carboxamide,
N-[2-(1H-benzimidazol-2-yl)phenyl]-trans-2-butenamide,
N-[2-(5-methoxy-1H-benzimidazol-2-yl)phenyl]-trans-2-butenamide,
N-[3-(5-methoxy-1H-benzimidazol-2-yl)phenyl]acetamide,
N-[3-(1H-imidazo[4,5-b]pyridin-2-yl)phenyl]acetamide, and
N-[3-(5-methoxy-1H-imidazo[4,5-b]pyridin-2-yl)phenyl] acetamide.

Additionally, compounds of Formula I also encompass all pharmaceutically acceptable acid addition salts and/or solvates, e.g., hydrates, thereof. The present invention also encompasses stereoisomers as well as optical isomers, e.g., mixtures of enantiomers as well as individual enantiomers and diastereomers, which arise as a consequence of structural asymmetry in certain compounds of Formula I. Separation of the individual isomers is accomplished by application of various methods which are well known to practitioners in the art.

The pharmaceutically acceptable acid addition salts of the invention are those in which the counter-ion does not contribute significantly to the toxicity or pharmacological equivalents of the bases of Formula I. They are generally preferred for medical usage.

In some instances, the salts have physical properties which make them more desirable for pharmaceutical formulation such as solubility, lack of hygroscopy, compressibility with respect to tablet formation and compatibility with other ingredients with which the substance may be used for pharmaceutical purposes.

The salts are routinely made by admixture of a Formula I base with the selected acid, preferably by contact in solution employing an excess of commonly used inert solvent(s) such as water, ether, benzene, methanol, ethanol, ethyl acetate or acetonitrile. They may also be made by metathesis or treatment with an ion exchange resin under conditions in which the anion of one salt of the substance of the Formula I substance is replaced by another anion under conditions which allow for separation of the desired species. Such conditions include precipitation from solution, extraction into a solvent and elution from/retention on an ion exchange resin.

Pharmaceutically acceptable acids for the purposes of salt formation of the substances of Formula I include sulfuric, phosphoric, hydrochloric, hydrobromic, hydroiodic, citric, acetic, benzoic, cinnamic, mandelic, phosphoric, nitric, mucic, isethionic, palmitic, heptanoic and others.

The compounds of the invention can be prepared using the following reaction schemes or modifications thereof that would be known to a skilled organic synthetic chemist. These schemes are meant only to be illustrative.

Scheme 1: (Acylation of 2-(2-aminophenyl)-1H-benzimidazole)

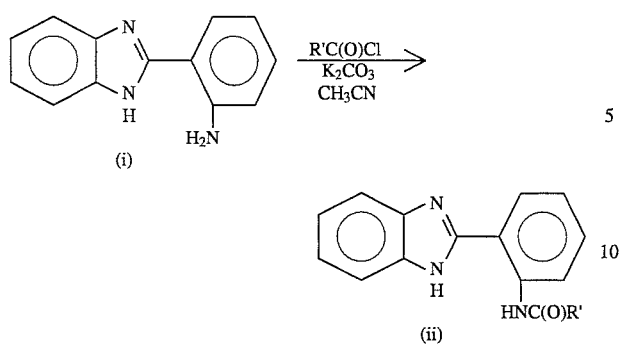

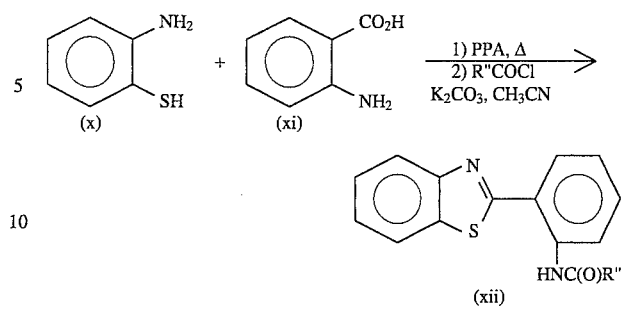

R'=$C_{2-4}$ alkyl, $C_{3-4}$ cycloalkyl, $C_{2-3}$ alkenyl, lower alkoxyalkyl, or lower alkylamino.

Scheme 2: (Preparation of N-alkyl ureas):

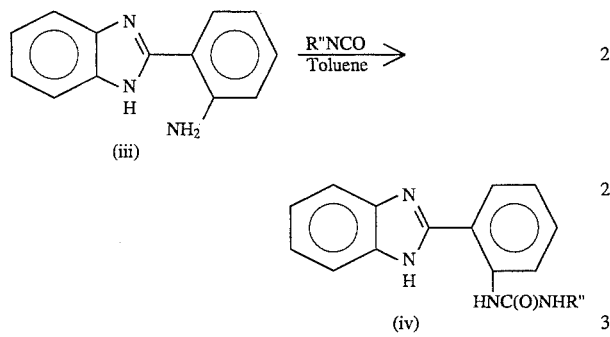

R''=$C_{1-4}$ alkyl

Scheme 3: (Benzoxazole Preparation)

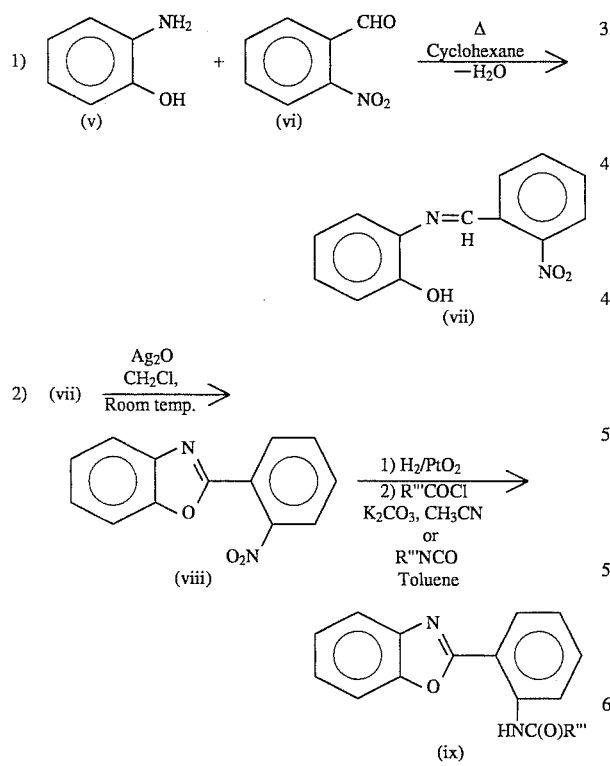

R'''=$C_{1-4}$ alkyl, or $C_{1-4}$ alkylamino

Scheme 4 (Benzthiazole Preparation):

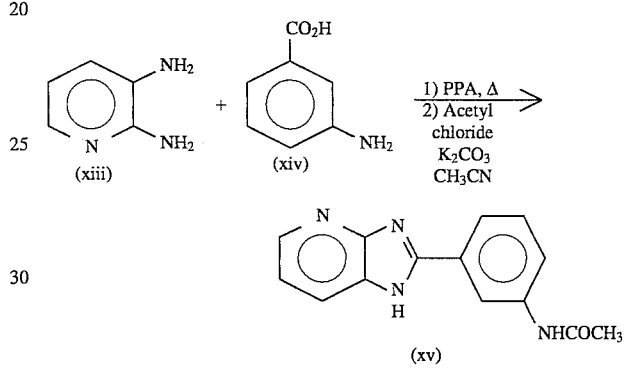

PPA=polyphosphoric acid

In the compound of Example 13, made using Scheme 4, R'' is $CH_3$.

Scheme 5 (Imidazopyridine):

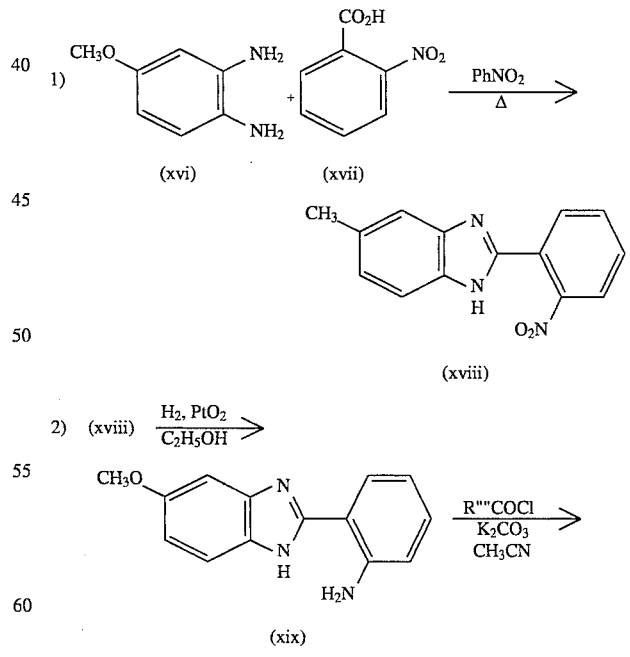

The compound of Example 14 was made using Scheme 5.

Scheme 6 (5-methoxybenzimidazoles):

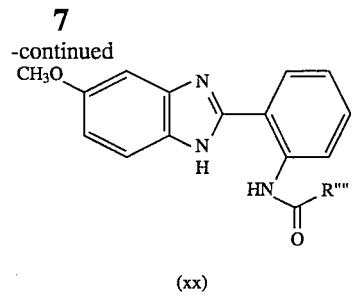

Typical R"" groups are $C_{1-4}$ alkyl and $C_{1-4}$ alkoxyalkyl groups, such as $CH_3$, $C_2H_5$, $CH_2OCH_3$, N-alkylamino, and the like.

The compounds of the invention may be administered to patients in need of anti-convulsive treatment in a variety of ways. Thus, oral, transdermal, subcutaneous, intravenous, intramuscular, rectal, buccal, intranasal and ocular routes can be used. Oral administration if preferred.

One or more of the compounds of the invention, or a salt thereof, is mixed with pharmaceutically acceptable amounts of one or more conventional pharmaceutical excipients to produce a formulation to be administered by the desired route. Generally, such formulations will contain one or several carriers or diluents. Useful carriers include solids, semi-solids and liquids which have miscibility, or other compatibility, with the active agent(s) so that they can deliver same to a patient or host.

Suitable carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate, mineral oil and the like. Mixtures are operable.

Other useful excipients include lubricants, wetting agents, gellants, emulsifiers, preservatives, colorants, perfumes, flavor enhancers, drying agents and the like. Mixtures can be employed.

Generally, compositions which include the compounds of the invention will contain from about 0.01 to about 10% of active compound(s) and 99.99 to 90%, or other suitable amounts, of excipient(s). However, compositions containing large amounts, e.g., about 1% to about 95% by weight of active compound(s), are contemplated.

The compositions are preferably formulated in a unit dosage form, each dosage containing from about 5 to 500 mg, more usually 25 to 300 mg, of the active ingredient. The term "unit dosage form" refers to physically discrete units suitable as unitary dosages for human subjects and other mammals, each containing a predetermined quantity of active material calculated to produce the desired therapeutic effect, in association with the required pharmaceutical carrier.

The active compounds are effective over a wide dosage range. For example, dosages per day will normally fall within the range of about 0.5 to 300 mg/kg, of body weight. In the treatment of adult humans, the range of about 1 to 50 mg/kg, in single or multiple doses, is preferred.

However, it will be understood that the amount of the compound actually administered, will be determined by a physician in light of the relevant circumstances including the condition to be treated, the choice of compound to be administered the chosen route of administration, the age, weight, and response of the individual patient, the severity of the patient's symptoms.

For treating epilepsy, a compound of Formula I may be employed as a daily dosage in the range of about 50 mg to about 2000 mg, usually in 1 to 4 divided dosages, for an average adult human. A unit dosage would contain about 2.5 mg to about 500 mg of the active ingredient.

In general, compounds of Formula I may be used in treating epilepsy in mammals, including humans, in a manner similar to that used for phenytoin. Medical aspects of the treating of epilepsy are described in greater detail by Rail and Schleifer in *Goodman and Gilman's The Pharmacological Basis of Therapeutics*, 8th ed.; Goodman Gilman, A.; Rail, T. W.; Nies, A. S.; Taylor, P., Eds., Pergamon Press: New York, 1990; pp. 436–462.

SPECIFIC EMBODIMENTS

The following examples illustrate the preparation of various compounds of the invention and their effectiveness as anticonvulsants and melatonergics.

Melting points were taken in Kimax soft-glass capillary tubes using a Thomas-Hoover Unimelt capillary melting point apparatus (Model 6406 K) and are uncorrected. Infrared spectra were recorded on a Perkin-Elmer 1800 Fourier Transform Infrared Spectrophotometer with peak positions given in reciprocal centimeters (cm$^{-1}$). $^1$H NMR spectra were obtained on a Bruker AC-300 NMR spectrometer equipped with a computer-switchable 5.0 mm $^1$H/$^{13}$C probe. Chemical shifts are reported in parts per million ($\delta$) downfield from tetramethylsilane. $^1$H NMR coupling constants (J values) are listed in Hertz (Hz) and spin multiplicities are reported as singlet (s), doublet (d), triplet (t), quartet (q), multiplet (m) and/or broad (b). Discharge chemical ionization (DCI) mass spectral data were acquired on a Finnegan 4500 quadrapole mass spectrometer equipped with a Vacumetrics discharge chemical ionization probe using isobutane reagent gas at 0.3 Torr source pressure. Microanalyses were acquired through the Analytical Department of The Bristol-Myers Squibb Company, Wallingford, Conn. Analytical thin-layer chromatography (TLC) was performed on 0.25 mm EM silica gel 60F-254 coated glass plates and preparative flash chromatography was performed on EM silica gel (32–62 mm). The solvent systems used are reported in each experimental. All reaction, extraction and chromatography solvents were reagent grade and used without further purification except tetrahydrofuran (THF) which was distilled from sodium/benzophenone ketyl. All non-aqueous reactions were carried out in flame-dried glassware under a nitrogen atmosphere. All commercially available reagents were used without further purification.

Unless otherwise noted, all percentages recited herein are weight percents, based on total composition weight.

A. Synthesis

EXAMPLE 1

N-[2-(1H-benzimidazol-2-yl)phenyl] propanamide

To a solution/suspension of 2-(2-aminophenyl) benzimidazole (5.0 g, 23.0 mmol), potassium carbonate (9.5 g, 69.0 mmol) in acetonitrile (300 mL) at 0° C. was added propionyl chloride (2.3 g, 23.0 mmol). The reaction mixture was allowed to warm to room temperature, stir overnight, followed by filtration to remove the white solid. This was washed thoroughly with acetonitrile. The acetonitrile was concentrated in vacuo, the residue extracted into methylene chloride, washed with potassium carbonate (saturated solution) and the organic layer was dried over anhydrous magnesium sulfate. The methylene chloride was removed in vacuo and the resulting solid was recrystallized from methanol, m.p. >200° C. $^1$H NMR (300 MHz, DMSO-d$_6$) δ13.14 (bs, 1H), 13.00 (s, 1H), 8.70 (d, J=8.4 Hz, 1H), 8.10 (d, J=8.0 Hz, 1H), 7.71 (d, J=7.2 Hz, 1H), 7.57 (d, J=8.3 Hz, 1H), 7.46 (t, J= 8.0 Hz, 1H), 7.31–7.20 (m, 3H), 2.53 (q, J=7.5 Hz, 2H), 1.23 (t, J=7.5 Hz, 3$^{13}$C NMR (75 MHz, DMSO-d$_6$) δ172.2, 150.9, 172.1, 138.4, 133.4, 130.7, 127.3, 123.5, 122.7, 122.3, 119.8, 118.6, 115.2, 111.5, 31.1, 9.6; IR (KBr)3262, 1662 cm$^{-1}$; MS (DCI) m/e MH$^+$=266; Analysis calc'd for $C_{16}H_{15}N_3O_1/0.4H_2O_1$: C, 70.53; H, 5.64; N, 15.37; H$_2$O$_1$, 2.40; found: C, 70.52; H, 5.84; N, 15.42; H$_2$O$_1$, 2.64.

The acylation technique of Example 1 is referred to as "General Procedure A" hereinafter.

EXAMPLE 2

N-[2-(benzimidazol-2-yl)phenyl] methoxyacetamide

Preparation was carried out according to Scheme 1 and General Procedure A using 2-(2-aminophenyl)benzimidazole and methoxyacetyl chloride. Purification was achieved by recrystallization from methanol, m.p. 229°–231° C. $^1$H NMR (300 MHz, DMSO-d$_6$) δ13.48 (s, 1H), 13.11 (bs, 1H), 8.80 (dd, J=9, 1.5 Hz, 1H), 8.10 (dd, J=1.5, 9 Hz, 1H), 7.63 (bm, 2H), 7.48 (dt, J=1.5, 6 Hz, 1H), 7.28 (m, 3H), 4.09 (s, 2H), 3.55 (s, 3H); $^{13}$C NMR (75 MHz, DMSO-d$_6$) δ169.26, 150.55, 137.58, 130.58, 127.43, 123.20, 122.81, 120.09, 116.10, 72.22, 59.34, two carbons obscured; IR (KBr) 3300–2600, 1650, 1550, 1125, 740 cm$^{-1}$; MS (DCI) m/e MH$^+$=282; Analysis calc'd for $C_{16}H_{15}N_3O_2$: C, 68.31; H, 5.37; N, 14.94; found: C, 68.52; H, 5.46; N, 14.96.

Some additional examples made according to Scheme 1 using General Procedure A are shown below in Table 1.

TABLE 1

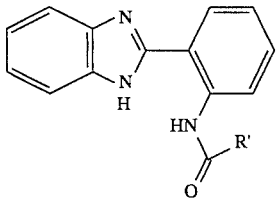

| Ex. | R' | Yield (%) | m.p. °C. |
|---|---|---|---|
| 3 | n-propyl | 28 | 214–216 |
| 4 | cyclopropyl | 14 | 235–236 |
| 5 | i-propyl | 13 | 202 |
| 6 | cyclobutyl | 31 | >210 |
| 7 | vinyl | 33 | >225 |
| 8 | CH=CHCH$_3$ | 3 | >225 |
| 9 | CH(CH$_3$)=CH$_2$ | 64 | 221–223 |

EXAMPLE 10

N-[2-(benzimidazol-2-yl)phenyl]-N'-methyl urea

This example illustrates Scheme 2. To a solution of 2-(2-aminophenyl)benzimidazole (5.0 g, 23.9 mmol) in toluene (300 mL) was added methyl isocyanate (1.5 mL, 26.0 mmol); the reaction mixture was allowed to stir overnight. The toluene was removed in vacuo to yield a yellow oil. This was purified by column chromatography using silica gel (20:1) in 5% MeOH/CH$_2$Cl$_2$. The product was isolated as a white solid (4.6 g, 72% yield), m.p. >220° C. $^1$H NMR (300 MHz, DMSO-d$_6$) δ12.9 (bs, 1H), 11.9 (s, 1H), 8.50 (d, J=8.4 Hz, 1H), 8.00 (d, J=7.9 Hz, 1H), 7.66 (s, 2H), 7.38 (t, J=8 Hz, 1H), 7.28–7.24 (m, 2H), 7.07 (t, J=7.4 Hz, 2H), 2.74 (d, J=3.5 Hz, 3H); $^{13}$C NMR (75 MHz, DMSO-d$_6$) δ155.80, 151.3, 140.3, 130.3, 127.1, 122.5, 120.4, 119.3, 114.1, 26.6, five carbons obscured; IR (KBr) 3344, 1672 cm$^{-1}$; MS (DCI) m/e MH$^+$=267; Analysis calc'd for $C_{15}H_{14}N_4O_1$: C, 67.65; H, 5.30; N, 21.04; found: C, 67.59; H, 5.24; N, 1.07.

EXAMPLE 11

N-[2-(benzoxazol-2-yl)phenyl] acetamide

The compound was prepared in a multistep synthesis employing Scheme 3, as described: A suspension of 2-aminophenol (5.0 g, 45.81 mmol) and 2-nitrobenzaldehyde (6.92 g, 45.81 mmol) in cyclohexane (200 mL) was heated to reflux using a Dean-Stark apparatus to remove water for 5 h. The reaction mixture was concentrated in vacuo to yield bright yellow crystals of the corresponding imine (10.71 g, 97% yield). To a solution of this imine (7.88 g, 32.56 mmol) in CH$_2$Cl$_2$ (200 mL) was added Ag$_2$O (9.05 g, 39.07 mmol) and the reaction mixture was allowed to stir at RT overnight. The solvent was removed in vacuo to yield a solid shown to be the 2-(2-nitrophenyl) benzoxazole. This product was then suspended in ethanol (200 mL) with PtO$_2$ (0.3 g) and charged with H$_2$ (60 psi). The reaction mixture was allowed to shake on a Parr apparatus for 3 h. This was filtered through celite and the filtrate was removed in vacuo to yield a yellow solid. $^1$H NMR showed this to be the desired 2-(2-aminophenyl) benzoxazole, 3.85 g. This was acetylated according to General Procedure A and purified by recrystallization from cyclohexane/ethyl acetate, m.p. 125°–128° C.; $^1$H NMR (300 MHz, DMSO-d$_6$) δ11.48 (s, 1H), 8.54 (d, J=9 Hz, 1H), 8.13 (dd, J=1.5, 9 Hz, 1H), 7.80–7.75 (m, 2H), 7.57 (m, 1H), 7.45 (m, 2H), 7.25 (t, J=9 Hz, 1H), 2.23 (s, 3H); $^{13}$C NMR (75 MHz, DMSO-d$_6$) δ5 168.79, 161.46, 148.92, 140.39, 138.59, 132.89, 128.62, 126.18, 125.28, 123.37, 120.29, 119.83, 113.05, 111.07, 25.15; IR (KBr) 3270, 1685, 1540, 1240, 750 cm$^{-1}$; MS (DCI) m/e MH$^+$= 253; Analysis calc'd for $C_{15}H_{12}N_2O_2$: C, 71.42; H, 4.79; N, 11.10; found: C, 71.24; H, 5.14;N, 10.76.

EXAMPLE 12

N-[2-(benzoxazol-2-yl)phenyl]-N'-methyl urea

This was prepared according to Scheme 3. To a solution of 2-(2amino)phenyl benzoxazole (1.6 g, 7.6 mmol) (preparation described in Example 12) was added methyl isocyanate (0.47 g, 8.31 mmol) in toluene. The reaction mixture was heated to a gentle reflux overnight. The solution was cooled and a white solid precipitated. This was collected by filtration, recrystallized from acetonitrile/methanol, dried in vacuo to give 0.132 g of a white solid, (7% yield), m.p. 226°–227° C. $^1$H NMR (300 MHz, DMSO-d$_6$) δ10.96 (bs, 1H), 8.48 (d, J=9 Hz, 1H), 8.09 (d, J=6 Hz, 1H), 7.78 (m, 2H), 7.45 (m, 3H), 7.35 (bs, 1H), 7.08 (t, J=6H 2.71 (bs, 3H); $^{13}$C NMR (75 MHz, DMSO-d$_6$) δ161.6, 155.3, 148.7, 140.7, 132.5, 128.1, 125.8, 125.0, 120.76, 119.5, 119.1, 110.91; IR (KBr) 3300, 1665, 1550, 1250, 750 cm$^{-1}$; MS (DCI) m/e MH$^+$=268; Analysis calc'd for $C_{15}H_{13}N_3O_2$: C, 67.41; H, 4.90; N, 15.72; found: C, 67.39; H, 4.85; N, 15.74.

EXAMPLE 13

N-[2-(benzthiazol-2-yl)phenyl] acetamide

This compound was prepared by multistep synthesis using Scheme 4 as follows: A paste of 2-aminothiophenol (2.0 g, 15.97 mmol) in polyphosphoric acid was prepared.

ortho-Anthranilic acid (2.91 g, 15.97 mmol) was added and the reaction mixture was heated at approximately 250° C. under a nitrogen atmosphere for 3 h. The reaction mixture was cooled to 175° C. and poured into rapidly stirring water. The solid which had formed was collected by filtration; it was washed with $K_2CO_3$ (sat'd sol'n), and dried in vacuo. $^1$H NMR (DMSO-$d_6$) and MS show the product to be the desired 2-(2-aminophenyl)benzthiazole. This material was acetylated according to General Procedure A and purified by recrystallization from cyclohexane/ethyl acetate, m.p. 124°–125° C. $^1$H NMR (300 MHz, DMSOd-$d_6$)δ11.83 (bs, 1H), 8.42 (d, J=8 Hz, 1H), 8.12 (m, 2H), 7.90 (dd, J=1,12 Hz, 1H), 7.52 (m, 3H), 7.24 (t, J=6 Hz, 1H), 2.19 (s, 3H); $^{13}$C NMR (75 MHz, DMSO-$d_6$) δ168.83, 167.46, 152.19, 137.29, 133.13, 131.82, 129.92, 126.80, 125.98, 123.82, 122.71, 122.05, 121.31, 119.99, 24.88; IR (KBr) 1690, 1540, 940, 740 cm$^{-1}$; MS (DCI) m/e MH$^+$=269; Analysis calc'd for $C_{15}H_{12}N_2O_1S_1$: C, 67.14; H, 4.51; N, 10.44; found: C, 67.12; H, 4.73; N, 10.51.

EXAMPLE 14

N-[3-(1H-imidazo[4,5-b]pyridin-2-yl)phenyl]acetamide

This compound was prepared according to Scheme 5. The amino precursor was prepared by heating 2,3-diaminopyridine (5.0 g, 45.8 mmol) and 3-aminobenzoic acid (6.28 g, 45.8 mmol) in PPA. The reaction was stirred at 200° C. for 3 h and poured into water. The resulting solid was collected by filtration and recrystallized from ethanol to yield 1.0 g of a beige solid which was shown to be the desired compound by $^1$H NMR. This was acetylated using General Procedure A. The final product was purified by recrystallization from methanol, m.p. >250° C. $^1$H NMR (300 MHz, DMSO-$d_6$) δ13.40 (s, 1H), 10.16 (s, 1H), 8.54 (bs, 1H), 8.30 (m, 1H), 7.99 (d, J=9 Hz, 1H), 7.84 (d, J=9 Hz, 1H), 7.69 (d, J=9 Hz, 1H), 7.47 (t, J=9 Hz, 1H), 7.22 (dd, J=6, 8 Hz, 1H), 2.08 (s, 3H); $^{13}$C NMR (75 MHz, DMSO-$d_6$) δ168.56, 152.71, 143.85, 139.92, 130.14, 129.38, 121.22, 121.08, 118.10, 117.55, 24.06, three carbons obscured; IR (KBr) 3400, 3260, 1635, 1550, 740 cm$^{-1}$; MS (DCI) m/e MH$^+$= 253; Analysis calc'd for $C_{14}H_{12}N_4O_1$: C, 66.66; H, 4.79; N, 22.21; found: C, 66.49; H, 4.88; N, 21.85.

EXAMPLE 15

N-[2-(5-methoxy-1H-benzimidazol-2-yl)phenyl]acetamide

This compound was prepared via Scheme 6 in a multistep synthesis as follows: 4-methoxy-l,2-phenylene diamine dihydrochloride (4.2 g, 30.43 mmol) was dissolved in NaOH (3N) and extracted with $CH_2Cl_2$. The organic layer was dried over $MgSO_4$ and the solvent removed in vacuo to yield an oil. $^1$H NMR showed the free base to be pure. To this was added nitrobenzene (100 mL), orthonitrobenzaldehyde (1.09 g, 7.24 mmol) and the reaction was heated overnight. The reaction mixture was cooled to RT and poured onto ethanolic HCl (7.2M). $Et_2O$ was added and a red solid precipitated. The precipitate was collected and dissolved in methanol, charcoal was added and the mixture was filtered. The methanol was concentrated on a steam bath and the product was allowed to precipitate as a beige solid. $^1$H NMR (DMSO-$d_6$) confirmed this to be 4-methoxy-2-(2-nitrophenyl) benzimidazole (3.89 g, 48% yield). This material (2.90 g, 12.1 mmol), along with $PtO_2$ (0.1 g) was suspended in EtOH (150 mL) and charged with $H_2$ (60 psi). The mixture was shaken for 1 h on a Parr hydrogenation apparatus; the mixture was filtered through a pad of celite and the solvent concentrated in vacuo to a yellow solid shown to be 4-methoxy-2-(2-aminophenyl)benzimidazole. This was acetylated according to General Procedure A and purified by recrystallization from methanol, m.p. 212°–213° C. $^1$H NMR (300 MHz, DMSO-$d_6$) δ mixture of conformational isomers, 8.66 (d, J=9 Hz, 1H), 8.05 (d, J=9 Hz, 1H), 7.61 (d, J=9 Hz, 0.5H), 7.44 (m, 1.5H), 7.28 (bs, 0.5H), 7.20 (t, J=7 Hz, 1H), 7.01 (d, J=1.5 Hz, 0.5H), 6.86 (m, 1H), 3.81 (s, 3H), 2.22 and 2.25 (s 3H); δ$^{13}$C NMR (75 MHz, DMSO-$d_6$) δ (mixture of conformational isomers), 168.43, 156.69, 155.81, 150.90, 149.95, 142.90, 138.23, 138.01, 136.55, 134.22, 130.35, 130.14, 127.81, 126.88, 122.64, 119.69, 119.25, 115.30, 113.46, 111.80, 100.87, 94.32, 55.48, 25.20; IR (KBr) 3300–2600, 2750, 1635, 1545, 1270, 815 cm$^{-1}$; MS (DCI) m/e MH$^+$=281; Analysis calc'd for $C_{16}H_{14}N_3O_2$: C, 68.56; H, 5.03; N, 14.99; found: C, 68.23; H, 5.42; N, 14.8.

EXAMPLE 16

N-[2-(5-methoxy-1H-benzimidazol-2-yl)phenyl] methoxyacetamide

Using Scheme 6, 4-methoxy-2-(2-aminophenyl)benzimidazole was prepared as described in Example 3. This was acylated with methoxyacetyl chloride using General Procedure A. Solid was recrystallized from hexane/ethyl acetate to give a white solid—0.100 g. (5% yield), m.p. 200°–201° C. $^1$H NMR (300 MHz, DMSO-$d_6$) δ13.44 (bs, 1H), 8.77 (dd, J=1.5, 9 Hz, 1H), 8.51 (dd, J=1.5, 9 Hz, 1H), 7.52 (d, J=9 Hz, 1H), 7.44 (t, J=9 Hz, 1H), 7.25 (t, J=9 Hz, 1H), 7.06 (d, J=2.4 Hz, 1), 6.88 (dd, J=2.4, 11.1, Hz, 1H), 4.08 (s, 2H), 3.78 (s, 3H), 3.54 (s, 3H); $^{13}$C NMR (75 MHz, DMSO-$d_6$) δ169.19, 156.27, 150.15, 137.27, 130.14, 127.13, 123.16, 120.03, 116.40, 112.25, 96.79, 72.24, 59.35, 55.50, three carbons obscured; IR (KBr) 3500–2500, 1670, 1550, 1300–1200, 1200–1100, 750 cm$^{-1}$; MS (DCI) m/e MH$^+$=312; Analysis calc'd for $C_{17}H_{17}N_3O_2$: C, 65.58; H, 5.50; N, 13.50; found: C, 65.72; H, 5.66; N, 13.10.

B. Biological Activity

The anticonvulsive properties of the compounds of the invention were evaluated using two standard animal models of epilepsy: the maximal electroshock test (MES) and the pentylenetetrazol (PTZ)-induced seizure procedure. Melatonergic action is indicated by binding studies done in hamster hypothalamus tissue.

1. Pentylenetetrazole—Induced Seizure Test

The PTZ technique employed was similar to that disclosed in P.C.T. publication WO 93/0572 (PCT/US92/07675), published on Apr. 1, 1993.

In the PTZ procedure, female C57Bl/6 mice (17–26 g) were injected j.p. (vol=0.1 ml/20 g) with test compound or vehicle 30 min before i.p. administration of 75 mg/kg pentylenetetrazol. Multiple doses of reference compounds (ethosuximide, trimethadione, and pentobarbital) were tested at the peak of activity and at the dose range reported in the literature. Ten mice were used per group. After injection, mice were placed in individual observation cages and monitored for one hour. During the first thirty minutes following PTZ injection, seizure activity was recorded by measure: the latency to the onset of pre-convulsive activity (Pre) the latency to the onset of the first clonic seizure longer than five seconds (First) the latency to the onset of the first intense-generalized clonic/tonic seizure (IGS) and the length of survival (Surv Time). During the second thirty-minute period, only time of death was recorded.

Those compounds that produced a significant delay in the onset of seizure activity or delayed (or abolished) mortality when compared to that produced by vehicle (reference) were classified as anticonvulsants. Significant differences between animals treated with reference or test compounds were determined using the Student's t-test.

2. Maximum Electroshock Test

The MES procedure used is based upon the tests disclosed by Swinyard and et al in *J. Pharmacol, Expt. Ther.*, (1952) 106, 319 and L. A. Woodbury et al in *Arch. Int. Pharmocodyn*, (1952), 92–97. These tests are also described in U.S. Pat. Nos. 5,242,942 and 5,240,937, respectively.

In the MES procedure, a tonic seizure was produced in female C57Bl/6 mice (17–26 g) by the delivery of a 50 milliamps current through corneal electrodes for 0.2 sec. Before testing, the animals were allowed food and water ad libitum. Compounds were injected i.p. 30 min before the MES. Reference compounds (phenytoin, carbamazepine, phenobarbital, and valproic acid) were tested at the peak of activity and at the dose range reported in the literature. Seven mice were used per group. In this test anticonvulsive activity was indicated by the abolition of the hind limb tonic extension. The median effective dose ($ED_{50}$) was obtained for each compound and compared to $ED_{50}$'s of reference compound(s).

The anticonvulsant properties of selected compounds of Formula I are shown in Table 2.

TABLE 2

Anticonvulsive Properties of Selected Formula I Compounds

| Ex. No. | MES** Results | PTZ Anti-Convulsive Results* | | | | |
|---|---|---|---|---|---|---|
| | | Pre | First | Surv Time | IGS | Surv |
| 1 | +++ | | | | | |
| 2 | ++ | | | | | |
| 10 | ++ | + | ++ | ++ | | ++++ |
| 11 | ++ | | | | | |
| 12 | + | + | +++ | ++ | + | ++ |
| 13 | +++ | | | | | |
| 15 | | + | + | ++ | | |

*50 mg/kg i.p. For PTZ results: + = >100% controls; ++ = >200% controls; +++ = >300% controls; ++++ = >400% controls
**For MES results: median effective dose ($ED_{50}$): + = <100 mg/kg; ++ = <75 mg/kg; +++ = <25 mg/kg
Pre: latency to first twitch
First: latency to first seizure
Surv Time: duration of survival
IGS: onset of intense, generalized seizures
Surv: survival at one hour post-PTZ
MES: maximum electroshock 3. Measurement of Melatonergic Binding Melatonin exerts its biological effects through specific receptors. Use of the biological active, radiolabelled agonist [$^{125}$I]-2-iodomelatonin has led to the identification of high affinity melatonin receptors in a variety of species. In the mammalian brain, autoradiographic studies have localized the distribution of melatonin receptors to a few specific structures. Although there are significant differences in melatonin receptor distribution even between closely related species, the highest binding site density generally occurs in discrete nuclei of the hypothalamus. In humans, specific [$^{125}$I]-2-iodomelatonin binding within the hypothalamus is completely localized to the suprachiasmatic nucleus, strongly suggesting that the melatonin receptors are located within the human biological clock.

The following studies employ hamster hypothalamus tissue and 2-[$^{125}$I]-iodomelatonin in assays to determine the melatonergic binding of the compounds tested.

1) Reagents:
   a) 50 mM Tris-HCl buffer pH 7.7 (20 C) using 10N NaOH
   b) $10^{-4}$ M 6-Chloromelatonin (diluted with 50% DMSO: 50% $H_2O$)
   c) 2-[$^{125}$I]iodomelatonin diluted to 0.1 nM final concentration Source: NEN Calculations: Concentration of stock:

Specific Activity = 2200 Ci/mMol
Concentration = 236 mCi/ml
Concentration of stock = $(236 \times 10^{-6}$ Ci/ml$)/$
$(2200$ Ci/mMol$) = 107.3$ nM
cpm/20 ml (conc.)(liters/tube) = $(1 \times 10^{-9\ m/L})\ (20 \times 10^{-6}L)$
= $2 \times 10^{-14}$ m
× by specific activity $(2 \times 10^{-11}$ mM$)(2200$ Ci/ mMol$)$
= $4.4 \times 10^{-8}$ Ci
× by decay factor $(4.4 \times 10^{-8})$ (1 on day made)
= $4.4 \times 10^{-8}$
× by dpm/Ci constant $(4.4 \times 10^{-8})(2.22 \times 10^{12}$ dpm/Ci$)$
= 97680 dpm
= 73260 cpm 2) Tissue Preparation: Male Golden Syrian hamsters are decapitated, the brains are rapidly removed and chilled. The hypothalamus is crudely dissected and frozen on dry ice with tissue stored at –80° C. until assayed. Tissue is weighed and thawed in 20 mls. ice cold Tris buffer (a) and homogenized by treatment with a polytron for 10 seconds at setting 17. Ice cold Tris (a) is added to a volume of 40 mls. The homogenate is centrifuged in a Sorvall-SS-34 head at 19,000 rpm (44,000×g) for 10 min. at 4° C. The resulting supernatant is decanted and discarded. The pellet is rehomogenized in an additional 20 mls of Tris-HCl, diluted and centrifuged as before. The supernatant is decanted and discarded. The resulting pellet is homogenized in 20 volumes of Tris-HCl per gram of original tissue (a 1:20 homogenate), chilled and held on ice until assayed.

3) Experimental Design:

| | Tube # | Buffer (a) | $10^{-4}$ M 6-Chloro melatonin | BMS Compound | 2-{$^{125}$I}-iodomelatonin | Tissue Homogenate (1:20) |
|---|---|---|---|---|---|---|
| Total | 1,2 | 20 ml | — | — | 20 ml | 160 ml |
| Blank | 3,4 | — | 20 ml | — | " | " |
| Unknowns: | 5,6 | — | — | 20 ml conc. 1 | " | " |
| | 7,8 | — | — | 20 ml conc. 1 | " | " |

4) Incubation: 0° C. (ice bath) for 1 hour. Tissue homogenate is added last to assay tubes (which are already in ice bath). 1 hour from addition of tissue 5 mls of cold buffer (a) are added to assay tubes and they are filtered using a Hoefer single-filter manifold. The filters are washed 2× with 5 mls of buffer.

5) Activity: Compounds with an $IC_{50}$ value less than 1000 nM are termed active.

For reference cf: Duncan, M. J., Takahashi, J. S. and Dubocovich, M. L. 2-[$^{125}$I]Iodomelatonin Binding Sites in Hamster Brain Membranes: Pharmacological Characteristics and Regional Distribution.

The melatonergic binding data for some selected compounds of Formula I are shown in Table 3.

TABLE 3

| Melatonergic Binding of Selected Formula I Compounds | |
|---|---|
| Ex. # | $IC_{50}$ (nM)* score |
| 1 | + |
| 4 | + |
| 8 | + |
| 12 | ++ |
| 13 | ++ |
| 14 | + |
| 15 | +++ |
| 16 | ++++ |

*$IC_{50}$(nM) is the nanomolar concentration giving displacement of 50% of radioactive label from melatonin binding sites in hamster hypothalamus tissue. Score: + = 100–600 nM; ++ = 25–100 nM; +++ = 10–25 nM; ++++ = <10 nM.

Reasonable variations, such as those which would occur to a skilled artisan, can be made herein without departing from the scope of the invention.

We claim:

1. A method of eliciting an anticonvulsive effect in a mammal in need thereof comprising the step of administering to said mammal an anticonvulsive amount of a compound of formula I or a pharmaceutically acceptable salt thereof:

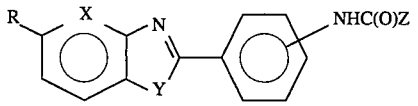

wherein
R=H or $C_{1-4}$ alkoxy;
X=CH or N;
Y=NH, O or S;
Z=$C_{1-4}$ alkyl, $C_{3-6}$ cycloalkyl, $C_{2-3}$ alkenyl, $NH_2$, $C_{1-4}$ alkylamino, or $C_{1-4}$ alkoxyalkyl, with the proviso that Z may not be $CH_3$ when R=H, X=CH, and Y=NH and Z may not be $CH_3$ when R=H, X=N and Y=NH and NHC(O)Z is in the para-position.

2. A method of eliciting an anticonvulsive effect in a mammal in need thereof comprising the step of administering to said mammal an anticonvulsive amount of a compound selected from the group consisting of:

N-[2-(1H-benzimidazol-2-yl)phenyl]-N'-methyl urea; N-[2-(5-methoxy-1H-benzimidazol-2-yl)phenyl] acetamide; N-[2-(benzimidazol-2-yl)phenyl]propanamide; N-[2-(benzoxazol-2-yl)phenyl]-N'-methyl urea; N-[2-(1H-benzimidazol- 2-yl)phenyl] methoxyacetamide; N-[2-(5-methoxy-1H-benzimidazol-2-yl)phenyl] methoxy acetamide; N-[3-(1H-imidazo[4,5-b]pyridin-2-yl)phenyl] acetamide; N-[2-(1H-benzimidazol-2-yl)phenyl] cyclopropane carboxamide; N-[2-(1H-benzimidazol-2-yl)phenyl]-trans-2-butenamide; N-[2-(benzimidazol-2-yl)phenyl] propanamide; and N-[2-(benzthiazol-2-yl)phenyl]acetamide.

3. The method of claim 2 wherein the compound is N-[2-(1H-benzimidazol-2-yl)phenyl]-N'-methyl urea.

4. The method of claim 2 wherein the compound is N-[2-(5-methoxy-1H-benzimidazol-2-yl)phenyl]acetamide.

5. The method of claim 2 wherein the compound is N-[2-(benzimidazol-2-yl)phenyl]propanamide.

6. The method of claim 2 wherein the compound is N-[2-(benzthiazol-2-yl)phenyl]acetamide.

7. The method of claim 2 wherein the compound is N-[2-(benzoxazol-2-yl)phenyl]-N'-methyl urea.

8. The method of claim 2 wherein the compound is N-[2-(1H-benzimidazol-2-yl)phenyl]methoxyacetamide.

9. The method of claim 2 wherein the compound is N-[2-(5-methoxy-1H-benzimidazol-2-yl)phenyl]methoxyacetamide.

10. The method of claim 2 wherein the compound is N-[3-(1H-imidazo[4,5-b]pyridin-2-yl)phenyl]acetamide.

11. The method of claim 2 wherein the compound is N-[2-(1H-benzimidazol-2-yl)phenyl]cyclopropane carboxamide.

12. The method of claim 2 wherein the compound is N-[2-(1H-benzimidazol-2-yl)phenyl]trans-2-butenamide.

13. A method of eliciting a melatonergic effect in a mammal in need thereof comprising the step of administering to said mammal a melatonergic amount of a compound of formula I or a pharmaceutically acceptable salt thereof:

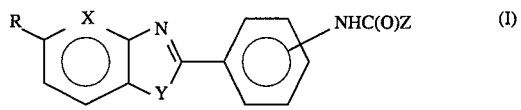

wherein
R=H or $C_{1-4}$ alkoxy;
X=CH Or N;
Y=NH, O or S;
Z=$C_{1-4}$ alkyl, $C_{3-6}$ cycloalkyl, $C_{2-3}$ alkenyl, $NH_2$, $C_{1-4}$ alkylamino, or $C_{1-4}$ alkoxyalkyl, with the proviso that Z may not be $CH_3$ when R=H, X=CH, and Y=NH and Z may not be $CH_3$ when R=H, X=N and Y=NH and NHC(O)Z is the para-position.

14. A method of eliciting a melatonergic effect in a mammal in need thereof comprising the step of administering to said mammal a melatonergic amount of a compound selected from the group consisting of:

N-[2-(1H-benzimidazol-2-yl)phenyl]-N'-methyl urea; N-[2-(5-methoxy-1H-benzimidazol-2-yl)phenyl] acetamide; N-[2-(benzimidazol-2-yl)phenyl]-propanamide; N-[2-(benzoxazol-2-yl)phenyl]-N'-methyl urea; N-[2-(1H-benzimidazol-2-yl)phenyl] methoxyacetamide; N-[2-(5-methoxy-1H-benzimidazol-2-yl)phenyl] methoxy acetamide; N-[3-(1H-imidazo[4,5-b]pyridin-2-yl)phenyl] acetamide; N-[2(1H-benzimidazol-2-yl)phenyl]cyclopropane carboxamide; N-[2-(1H-benzimidazol-2-yl)phenyl]-trans-2-butenamide; N-[2-(benzimidazol-2-yl)phenyl] propanamide; and N-[2-(benzthiazol-2-yl)phenyl] acetamide.

15. The method of claim 14 wherein the compound is N-[2-(1H-benzimidazol-2-yl)phenyl]-N'-methyl urea.

16. The method of claim 14 wherein the compound is N-[2-(5-methoxy-1H-benzimidazol-2-yl)phenyl]acetamide.

17. The method of claim 14 wherein the compound is N-2-benzimidazol-2-yl)phenyl]propanamide.

18. The method of claim 14 wherein the compound is N-[2-(benzthiazol-2-yl)phenyl]acetamide.

19. The method of claim 14 wherein the compound is N-[2-(benzoxazol-2-yl)phenyl]-N'-methyl urea.

20. The method of claim 14 wherein the compound is N-[2-(1H-benzimidazol-2-yl)phenyl]methoxyacetamide.

21. The method of claim 14 wherein the compound is N-[2-(5-methoxy-1H-benzimidazol-2-yl)phenyl]methoxyacetamide.

22. The method of claim 14 wherein the compound is N-[3-(1H-imidazo[4,5,b]pyridin-2-yl)phenyl]acetamide.

23. The method of claim 14 wherein the compound is N-[2-(1H-benzimidazol-2-yl)phenyl]cyclopropane carboxamide.

24. The method of claim 14 wherein the compound is N-[2-(1H-benzimidazol-2-yl)phenyl] -trans-2-butenamide.

* * * * *